United States Patent [19]

Wang

[11] Patent Number: 5,670,366

[45] Date of Patent: Sep. 23, 1997

[54] RECOMBINANT DNA SEQUENCES ENCODING PHOSPHOLIPASE

[75] Inventor: Xuemin Wang, Manhattan, Kans.

[73] Assignee: Kansas State University Research Foundation, Manhattan, Kans.

[21] Appl. No.: 471,251

[22] Filed: Jun. 6, 1995

[51] Int. Cl.⁶ .................. C12N 1/20; C12N 9/22; C12N 15/00; C12P 21/06
[52] U.S. Cl. ............... 435/252.33; 435/69.1; 435/71.2; 435/199; 435/320.1; 536/23.2; 536/23.6; 530/350; 530/370
[58] Field of Search ................ 435/199, 198, 435/69.1, 68.1, 69.7, 252.3, 240.2, 252.33; 536/23.2, 23.4, 23.6

[56] References Cited

PUBLICATIONS

Billah, M.M. (1993) *Current Opinion in Immunology* 5, 114–123.
Brown, H.A., Gutowski, S., Moomaw, C.R., Slaughter, C., and Sternweis, P.C. (1993) *Cell* 1993, 75, 1137–1144.
Cockroft, S., Thomas, G.M.H., Fensome, A., Geny, B., Cunningham, E., Gout, I., Hiles, I., Totty, N.F., Truong, O., and Hsuan, J.J. (1994) *Science* 263, 523–526.
Liscovitch, M. (1992) *Trends in Biochem. Sci.* 17, 393–399.
Herman, E.M., and Chrispeels, M.J. (1980) *Plant Physiol.* 66, 1001–1007.
Lee, M.H. (1989) *Plant Sci.* 59, 35–43.
Borochov, A., Halevy, A., and Shinitzky, M. (1982) *Plant Physiol.* 69, 296–299.
Brown, J. H., Chamber, J.A., and Thompson, J. E. (1990) *Phytochem.* 30, 2537–2542.
Willemot, C. (1983) *Phytochem.* 22, 861–863.
Voisine, R., Vezina, L-P., and Willemot, C. (1993) *Plant Physiol.* 102, 213–218.
Wang, X. (1993) in *Lipid Metabolism in Plants.* (Moore, T.S. ed) pp. 499–520, CRC Press, Boca Raton.

Heller, M. (1978) *Adv. Lipid Res.* 16, 267–326.
Wang, P., Athens, J.C., Sigel, M.I., Egan, R.W., and Billah, M.M. (1991) *J. Biol. Chem.* 266, 14877–14880.
Dyer, J.H., Ryu, S.B., and Wang, X. (1994) *Plant Physiol.* 105, in press.
Heller, M., Mozes, N., Peri, I., and Maes, E. (1974) *Biochim. Biophy. Acta* 369, 397–410.
Allgyer, T.T., and Wells, M.A. (1979) *Biochem.* 24, 5348–5353.
Wang, X., Dyer, J.H., and Zheng, L. (1993) *Arch. Bichem. Biophys.* 306, 496–494.
Abousalham, A., Reviere, M., Teissere, M., and Verger, R. (1993) *Biochim Biophys. Acta* 1158, 1–7.
Wang, X., Bookjans, G., Altsuler, M., Collins, G.B. and Hildebrand, D.F. (1988) *Physiol. Plant.* 72, 127–132.
Touchstone, J.C. Levin, S.S. Dobbins, M.F., and Carter, P.J. (1981) *J. High Res. Chrom. & Chrom. Commun.* 4, 423–424.
Heidecker G. and Messing J. (1986) *Ann. Rev. Plant Physiol.* 37, 439–466.
Lutcke H.A., Chow, K.C., Mikcel, F.S., Moss, K.A., Kern H.F. and Sheele, G.A. (1987) *EMBO J.* 6, 43–48.
Aitken, A. (1990) *Identification of Protein Consensus Sequences: active site motifs, phosphorylation, and other post–translational modifications*, Ellis Horwood, London.
Kyte, J. and Doolittle, R.F. (1982) *J. Mol. Biol.* 157, 105–132.

(List continued on next page.)

*Primary Examiner*—Robert A. Wax
*Assistant Examiner*—Tekchand Saidha
*Attorney, Agent, or Firm*—Hovey, Williams, Timmons & Collins

[57] ABSTRACT

Substantially isolated and purified eukaryotic nucleotide sequences encoding for plant phospholipases (e.g., phospholipase D) are disclosed which can be inserted into an expression vector and used for the recombinant expression of substantially purified phospholipases. An exemplary phospholipase D cDNA clone contains a 2424-bp open reading frame encompassing 808 amino acids.

24 Claims, 2 Drawing Sheets

OTHER PUBLICATIONS

Pearson, W. and Lipman, D. (1988) *Proc. Natl. Acad. Sci. USA* 85, 2444–2448.

Saito, M., Bourque, E., and Kanfer, J. (1974) *Arch. Biochem. Biophys.* 164, 420–428.

von Heijne, G., Steppuhn, J., and Herrmann, R.G. (1989) *Eur. J. Biochem.* 180, 535–545.

Scallon, B.J., Fung, W.–J., Tsang, T.S., Li, S., Kado–Fong, H., Huang, K.–S., and Kochan, J.P. (1991) *Science* 252, 446–448.

Hodgson, A.L.M., Bird, P., and Nisbet, L.I. (1990) *J. Bacteriol.* 172, 1256–1261.

Acharya, M.K., Dureja–Munjal, I., and Guha–Mukherjee, S. (1991) *Phytochem.* 30, 2895–2897.

Ueki,J., Morioka,S., Komari,T. & Kumashiro, T. (1995) Plant Cell Physiol. 36(5), 903–914. (1995).

Wang,X., Xu,L & Zheng,L. (1994) J. Biol. Chem. 269(32), 20312–20317. Aug. 12, 1994.

Wang,X., Dyer,J. & Zheng, L. (1993) Arch. Biochem. Biophys. 306(2), 486–494. Nov. 1, 1993.

5,670,366

RECOMBINANT DNA SEQUENCES ENCODING PHOSPHOLIPASE

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The present invention is broadly concerned with DNA nucleotide sequences which encode for plant phospholipases (e.g., phospholipase D) expression vectors (e.g., plasmids) including such sequences, and recombinantly-derived and substantially purified plant phospholipases such as phospholipase D able to catalyze hydrolysis and transphosphatidylation reactions.

2. Description of the Prior Art

Plant phospholipases are enzymes found in a wide variety of plant species, and are believed to be functionally important. Phospholipase D (PLD; EC 3.1.4.4) is one type of plant phospholipase which hydrolyzes phospholipids at the terminal phosphorus ester bond, leading to the formation of phosphatidic acid (PA) and the free hydrophilic alcohol substituent. In animals, a great deal of evidence now points to the receptor-linked hydrolysis of phospholipids by intracellular PLD (Ref 1). The PLD hydrolysis of phospholipids, especially phosphatidylcholine (PC), has been observed within seconds or minutes in response to a variety of agents including hormones, neurotransmitters, growth factors, and phorbol esters. PA has been shown to stimulate DNA synthesis, cell proliferation, and a number of signal transducing enzymes such as phosphatidylinositol 4, 5 bisphosphate-phospholipase C and phosphatidylinositol phosphate kinase. PA can also be converted by PA phosphohydrolase to diacylglycerol, a known activator of protein kinase C. Recent studies suggest the involvement of PLD in membrane traffic via the ADP-ribosylation factor signaling system (2, 3). PLD is also thought to be an integral part of the signaling network involving various phospholipases (4).

PLD activity is widespread in the plant kingdom. Changes in PLD activity associated with membrane phospholipid content have been described in relation to lipid catabolism in seed germination, lipid turnover and lipid composition changes during plant development, and membrane deterioration in stress injuries (5–10). Reports also exist concerning the involvement of PLD and PC hydrolysis in response to various stimuli such as light, temperature, hypoosmotic shock, hormones, and pathogenesis (11, 12 and refs therein). It is unknown, however, whether or not the PLD activity in plants plays a role in the sequence of events in signal transduction, as in animal systems. In terms of biochemical properties, a number of parallels between plant and animal PLDs have been noted. PLDs from both sources have been found in soluble and membrane fractions (13, 14). In the presence of primary alcohols, PLDs of plants and animals also catalyze a transphosphatidylation reaction in which the phosphatidyl moiety is accepted by an alcohol to form phosphatidylalcohol (13). While PLD may hydrolyze phospholipids with various head groups, PC, the major phospholipid in eukaryotic membranes, is often the preferred substrate for PLD of various sources (1, 13). Multiple forms of PLD have been demonstrated in plants and also suggested in mammalian tissues (14, 15).

Crucial to understanding of the role of PLD in cellular processes are the modes of regulation and activation of this enzyme in the cell. Such studies will be greatly facilitated by the availability of the PLD gene, but so far cloning of PC-hydrolyzing PLD has not been reported from any organism. In animals, the use of conventional cloning methods (e.g. PLD purification followed by generation of specific antibodies and/or amino acid sequences for library screening) has been hindered because purification of PLD has proven to be difficult. Although the purification of PLD from plants was described as early as in the 1970's (16, 17), immunological analysis using anti-PLD antibodies and partial amino acid sequences have only been reported recently (18, 19).

Because of its importance in cellular metabolism, PLD can be manipulated to improve various biological products. However, such improvement has not been possible due to the lack of the DNA sequence information on phospholipase D. Furthermore, because of its specificity in hydrolyzing phospholipids and the resultant production of phosphatidic acid and transphosphatidyl derivatives, PLD can be an important chemical reagent. However, owing to the difficulty of obtaining purified PLD directly, PLD has been unavailable at a reasonable price. Accordingly, there is an unsatisfied need in the art for a relatively low cost source of PLD.

In addition, no other plant phospholipases of class a1, a2, b or c has been purified to homogeneity and cloned. Phospholipase a2 enzymes have been shown to be involved in the mechanism of novel fatty acid biosynthesis, for example in ricinoleic acid and vernolic acid biosynthesis. An understanding of how these and related phospholipases function is important in attempts to express commercial amounts of novel fatty acids in temperate oilseed crops such as canola, linseed, soybean and sunflower. It is likely that such plant phospholipases are members of gene families related to PLD with substantial nucleic acid homology.

SUMMARY OF THE INVENTION

The present invention overcomes the problems outlined above and provides substantially isolated and purified eukaryotic complementary DNA sequences (i.e., cDNAs) which encode for plant phospholipases such as phospholipase D, and particularly phosphatidylcholine-hydrolyzing phospholipase D. Such DNA sequences preferably consist essentially of DNA sequences encoding for plant phospholipases. A particular sequence encoding for PLD is derived from castor bean (*Ricinus communis*) and comprises a 2424-bp open reading frame sequence between nucleotides 171 and 2595 of SEQ ID #1. However, the invention also embraces sequence having sufficient similarity to the aforementioned open reading frame to code for related plant phospholipases. Generally speaking, such sufficient similarity should comprise at least about 50% identity of nucleotides (homology), and more preferably about 70% identity.

The invention also provides expression vectors including therein genetic inserts having nucleotide sequences coding for plant phospholipases in host organisms. Preferably, such vectors comprise a plasmid which can be introduced into a host organism such as *E. coli*. Such transformed cells including a recombinant DNA molecule such as a plasmid are also within the ambit of the invention.

Additionally, the invention provides recombinantly-derived plant phospholipases such as phospholipase D. An exemplary phospholipase D is made up of 808 amino acids as specified in SEQ ID #2. Those skilled in the art will understand, however, that the invention also includes similar or analogous plant phospholipases, particularly those having greater than 50% (preferably greater than 70%) amino acid residue identity as compared with SEQ ID #2. Such phospholipases could include those of classes a1, a2, b and c which could have functionalities in various aspects of metabolism including fatty acid biosynthesis.

DESCRIPTION OF THE PREFERRED EMBODIMENTS

Figure 1:
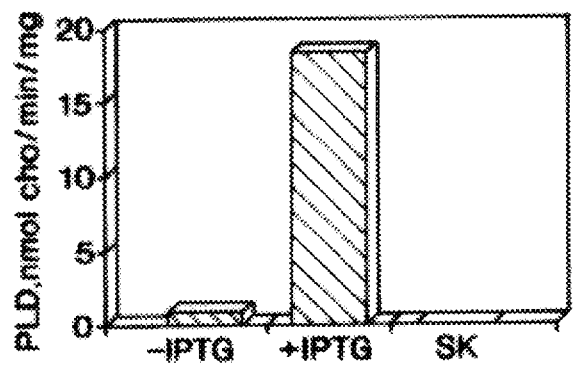
FIG. 1 is a graph illustrating PLD activity measured by the release of [$^3$H] choline from dipalmitoyl-glycero-3-P-[methyl-$^3$H]-choline by cell free extract of *E. coli* JM109 transformed with pBluescript SK alone or SK harboring the PLD cDNA clone, where + and −IPTG indicates the protein extracts from JM109 with the cDNA clone in SK grown in the presence or absence of IPTG, respectively.

The following example describes the sequencing of PLD cDNA and expression of PLD using the cDNA insert. It is to be understood that this example is provided by way of illustration only and nothing therein should be taken as a limitation upon the overall scope of the invention. The references referred to herein are incorporated by reference.

MATERIALS AND METHODS

PLD Purification, Sequencing and Antibodies

PLD was purified from 2-d postgermination endosperm of castor bean (*Ricinus communis* L. var. Hale) (18). After electrophoresis in an SDS/8% polyacrylamide minigel, the protein was electroblotted onto a polyvinylidine difluoride membrane with 0.195M glycine/25 mM Tris as the transfer buffer. The membrane filter was stained with 0.1% Coomassie blue in 40% methanol for 2 min followed by destaining with 40% methanol for 3 min. The PLD band was excised and sequenced up to 25 amino acid residues using an automated gas-phase protein sequenator. Anti-PLD antibodies were raised in rabbits using the purified PLD as antigen (18).

Isolation of PLD cDNA Clones

Two degenerate oligonucleotides were synthesized based on the N-terminal amino acid sequence: a 29mer GARGARACNGTNGGNTTYGGNAARGGNGT (SEQ ID #3) and a 20mer YTNTAYGCNACNATNGAKYT (SEQ ID #4), wherein N is inosine, R is A or G, Y is T or C, and K is T or G. The 5' ends of the degenerate 29mer and 20mer were $^{32}$P-labelled with T$_4$ polynucleotide kinase. A λUniZap cDNA library from castor bean endosperm after 3 d imbibition was generously provided by Sean Coughlan (Pioneer Hi-Bred International). The cDNA library was transformed into *E. coli* strain XL1. Plaques were transferred onto nylon filters in duplicate. The filters were hybridized with $^{32}$P-labelled oligonucleotides in a solution of 6X SSC, 10 mM (Na)$_3$PO$_4$, 1 mM EDTA, 0.5% SDS, 0.1% nonfat dried milk, and 50 μg/ml denatured salmon sperm DNA for 18 hours. The hybridization temperatures were 59° C. and 40° C. for the 29mer and 20mer, respectively. After hybridization, the filters were washed 3 times (5 min each) with a washing solution of 3X SSC and 0.1% SDS at room temperature followed by one wash at the hybridization temperature with the same solution. Plaque purification was carried out to isolate the positive clones.

DNA Sequencing

The cDNA insert from the positive clone was digested with various restriction enzymes and the fragments were subcloned into the pBluescript plasmids, SK and/or KS. The complete DNA sequence was determined by using Sequenase 2 kit according to the manufacturer's instruction (US Biochemicals). Vector pBluescript-based primers, universal forward and reverse, T$_3$, T$_7$, SK, and KS, were used in most sequencing reactions. PLD cDNA-based primers were also synthesized for clarifying the ambiguities. The final sequence was determined from both strands. Comparison of PLD nucleic acid and amino acid sequences with other sequences and other analyses were done with the Genetics Computer Group software (University of Wisconsin).

Expression of PLD cDNA in *E. coli*

The excised cDNA insert in the pBluescript SK(−) was transformed into *E. coli* JM 109. Fifty microliter of the overnight cultures of transformants were added to 25 ml LB medium with 50 μg/ml ampicillin. The cells were incubated at 37° C. with shaking for 3 hours, and then IPTG (isopropyl-1-thio-β-D-galactopyranoside) was added to a final concentration of 2 mM. The induced cells were cultured at 30° C. overnight and harvested with centrifugation at 6,000 g for 10 min. The cells were resuspended in the buffer containing 50 mM Tris-HCl (pH 8.0), 150 mM NaCl, 0.25 mM phenylmethylsulfonyl fluoride, 2 mM EDTA, and then pelleted by centrifugation. The cells were lysed by sonication in the resuspension buffer and cell debris were removed by centrifugation at 10,000 g for 5 min. Proteins in the supernatant were assayed for PLD activity and also subjected to PAGE followed by immunoblot analysis using anti-PLD antibodies.

To express PLD without the 30 amino acid N-terminal leader sequence, oligonucleotides with added EcoRI site were used as primers for polymerase chain reaction. The PLD cDNA in SK plasmid served as the template for PCR (polymerase chain reaction). The PCR mixture (100 μl) contained 10 ng of the template DNA, 2.5 mM MgCl$_2$, 0.2 mM dNTP, and 100 pmoles of each primer. The thermocycle profiles for the PCR were: 2 cycles, 92° C., 2 min/42° C., 1 min/72° C., 1 min; 30 cycles, 92° C., 1 min/42° C., 30 s/72° C., 30 s; 2 cycles; 92° C., 1 min/42° C., 30 s/72° C., 6 min. The resulting fragment was digested with EcoRI and electrophoresed on a 1% agarose gel. The band was excised, eluted, and ligated with the expression vector pGEX-2T (Pharmacia) containing glutathione S-transferase fusion protein. The ligated plasmid was transformed into *E. coli* JM 109. The procedures for PLD induction and lysate preparation were the same as above. The glutathione S-transferase fusion polypeptide was cleaved with human plasma thrombin (0.5 unit/ml) at room temperature for 1 hour.

Northern Blot Analysis

Castor bean RNA was isolated using a cetyltrimethylammonium bromide extraction method as described previously (20). Total RNA was subjected to denaturing formaldehyde/agarose gel electrophoresis, and transferred onto a nylon membrane. After transfer, the RNA was fixed on the filters by crosslinking by UV illumination. Northern blots were prehybridized in a solution of 6X SSC, 0.5% SDS, and 100 μg/ml salmon sperm DNA at 68° C. The probe was the 2834-bp EcoRI-Kpn1 fragment labelled with [α-$^{32}$P]dCTP by random priming. Hybridization were performed in the same solution at 68° C. overnight. The blots were washed with 1X SSC and 0.1% SDS followed by 0.2X SSC and 0.1% SDS at 68° C. and exposed to X-ray film.

PLD Activity Assay

The assay reaction mixture contained 100 mM MES (4-morpholineethanesulfonic acid), pH 6.5, 25 mM $CaCl_2$, 0.5 mM SDS, 1% (v/v) ethanol, 2 mM PC (phosphatidylcholine, egg yolk) containing dipalmitoylglycero-3-phospho[choline-methyl-$^3$H] choline. Detailed procedures for the substrate preparation, reaction conditions, and product separation were previously described (18). The release of [$^3$H] choline into aqueous phase was quantitated by scintillation counting. The hydrolysis and transphosphatidylation products, PA (phosphatidic acid) and phosphatidylethanol respectively, were analyzed by TLC. The lipids were made visible by spraying the chromatogram with 10% $CuSO_4$ in 8% phosphoric acid followed by heating the plate at 170° C. for 10 min (21).

RESULTS

Isolation and Nucleotide Sequence of PLD cDNA Clones

The castor bean cDNA library was first screened using the 29mer as probe. A number of positive clones with different signal to noise ratios were isolated and then screened with the 20mer. The clones that hybridized with both probes were analyzed further to confirm their identity. The cDNA inserts of these clones were excised in vivo with the helper phage R344 (Stratagene) to the pBluescript SK (−). Approximately 300 bases from both ends of these cDNA inserts were sequenced by the dideoxynucleotide method using SK and universal reverse primers. The deduced amino acid sequence from one clone matched perfectly with the N-terminal amino acid sequence determined from the purified PLD, and the full DNA sequence of this clone was determined.

The 2834-bp cDNA clone (SEQ ID #1) contains a 2424-bp open reading frame between nucleotide 171 and 2595, encompassing 808 amino acids (SE ID #2). The ATG codon at the position 171 is most likely to be translation initiation because it is in the same open reading frame as the N-terminal sequence of PLD determined from direct sequencing of the purified PLD and is immediately preceded by a termination codon. In addition, the sequence surrounding the ATG (AGAAATGGC) conforms closely to the known consensus sequence (AACAATGGC) for the initiating methionine in plants (22). A consensus sequence of polyadenylation signal [(A or U)AAUAA) was observed starting at the position 2659 of the 3' untranslated region. This position relative to the poly(A)$^+$ tail appears to be remote since the polyadenylation signal typically precedes the end of the message by 15 to 30 nucleotides (23). At the position 20 bases upstream from the start of the poly(A)$^+$ tail, a sequence (UAAUCCA) partially resembling the consensus sequence was observed, which is the probable polyadenylation signal for the PLD mRNA. It should be noted that although the consensus polyadenylation signal has been identified in some plant genes, unlike the highly conserved counterpart in animals, the plant signal sequence is not well conserved and sometimes even absent (22).

Expression of Castor bean PLD in E. coli

To confirm the identity of the PLD clone, the pBluescript SK harboring the 2834-bp cDNA insert (SEQ ID #1) was used for PLD protein induction. Addition of IPTG induced the synthesis of soluble and functional PLD. Cell extracts from *E. coli* JM 109 containing pBluescript alone did not contain detectable PLD activity under the present assay conditions. The cDNA insert in the vector produced a trace level PLD activity without IPTG induction. After addition of IPTG, approximately 20-fold increase in PLD activity was observed in the cell extract. As with the PLD activity found in the castor bean extract, the expressed PLD catalyzes both the hydrolysis and transphosphatidylation reactions.

In particular, the FIG. 1 graph represents PLD activity measured by the release of [$^3$H] choline from dipalmitoyl-glycero-3-P-[methyl-$^3$H]-choline by cell free extract of *E. coli* JM109 transformed with pBluescript SK alone or SK harboring the PLD cDNA clone. + and −IPTG indicates the protein extracts from JM109 with the cDNA clone in SK grown in the presence or absence of IPTG, respectively. IPTG was also added to the SK without the PLD cDNA insert. The FIG. 2 photograph depicts TLC analysis of hydrolysis and transphosphatidylation products produced by the expressed PLD in *E. coli* extracts. PLD activity was assayed in the presence of 1% ethanol. Lanes 1, transformed with SK; 2, transformed with pGEX-2T containing the PLD cDNA without the 30 amino acid leader peptide; 3 and 4, transformed with the full length PLD cDNA which are un-induced and induced with IPTG, respectively; 5, PLD from the extract of 2-d postgermination castor bean endosperm; 6 and 7, standard phosphatidylethanol (PEt) and phosphatidic acid (PA), respectively, (Avanti Polar Lipids Inc.). The lipids were made visible by spraying the chromatogram with 10% $CuSO_4$ in 8% phosphoric acid followed by heating the plate at 170° C. for 10 min (21).

Soluble extracts derived from cultures of either induced or un-induced cells containing the SK plasmid were tested for the PLD polypeptide by probing the Western blot with anti-PLD antibodies. Only the IPTG-induced extract is immunopositive and no truncated or partially degraded PLD was detected on the protein immunoblot.

Figure 3A:
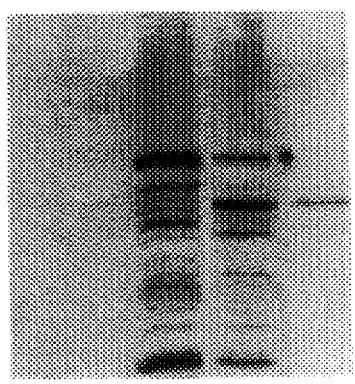
FIG. 3A is a photograph illustrating an immunoblot analysis of PLD expressed in *E. coli*.
Figure 3B:
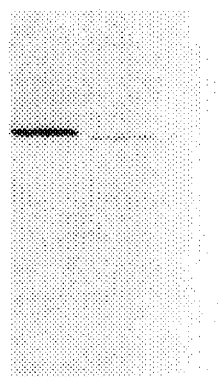
FIG. 3B is a photograph illustrating an immunoblot analysis of PLD extracted from two-day postgermination castor bean endosperm (lane 1) and as recombinantly expressed using the full-length PLD cDNA of SEQ ID #1 (lanes 2 and 3)

Specifically, crude protein extract (12,000 g supernatant) of transformed *E. coli* was separated by SDS-PAGE on 8% gels, transferred to polyvinylidine difluoride membranes, and probed with anti-PLD antibodies. These results are shown in FIG. 3A wherein: Lane 1, transformed with SK; 2 and 3, IPTG uninduced and induced cells, respectively, transformed with pGEX-2T containing the PLD cDNA without the 30 amino acid leader peptide; 4, the same extract as the lane 3 treated with human thrombin; 5, transformed with the full length PLD cDNA. The asterisk indicates the PLD-glutathione S-transferase fusion protein. In FIG. 3B: Lanes 1, PLD from the extract of 2-d postgermination castor bean endosperm; 2 and 3, IPTG induced and un-induced cells, respectively, transformed with the full length PLD cDNA. The gel A was run for a prolonged period to enhance the separation of the PLD-glutathione S-transferase fusion protein from the PLD, and thus proteins smaller than 35 kD were run off the gel.

Figure 2:
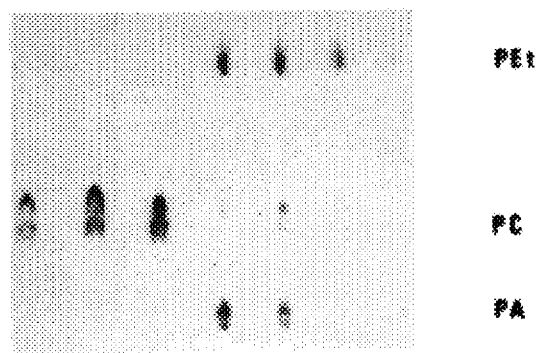
FIG. 2 is a photograph illustrating the results of a thin layer chromatography analysis of the hydrolysis and transphosphatidylation products produced by the expressed PLD in *E. coli* extracts.

Comparison of the deduced protein sequence (SEQ ID #2) to the N-terminal amino acid sequence of the purified castor bean PLD revealed that the translation product contained a leader peptide of 30 amino acids. To gain insights into the role of the peptide, a PCR DNA fragment without the first 261 nucleotides was ligated with pGEX-2T vector to express PLD without the 30 N-terminal amino acid leader sequence. This plasmid was then expressed in *E. coli* JM 109, producing a PLD (minus the first 30 amino acids) fused to glutathione-S-transferase. The fusion protein was recognized by anti-PLD antibodies as shown in FIG. 3A. There also appeared a number of smaller immunopositive bands which were absent in the cell free extract of the same plasmid without IPTG induction, suggesting partial degradation of the expressed PLD in *E. coli*. After cleavage of the fusion protein with thrombin, a new immunoreactive band with a molecular weight similar to that of the PLD expressed from the full length cDNA was visible on the immunoblot, indicating the release of the PLD polypeptide from the fused glutathione S-transferase. In contrast to the PLD expressed using the full length cDNA, the PLD expressed without the leader sequence showed no catalytic activity either before or after thrombin cleavage of PLD from the fusion protein (FIG. 2).

Sequence Analysis

The deduced amino acid sequence of the open reading frame corresponds to a protein of 808 amino acids with a predicted molecular weight of 92,386 and pI of 5.7. Excluding the first 30 N-terminal amino acids which are absent in mature PLD, the predicted molecular weight is 89,000, and the estimated pI is 5.5. The molecular weight of the purified castor bean PLD was estimated at 92,000 from SDS-gels, which is in agreement with that deduced from the full length cDNA and is 3,000 larger than the mature PLD predicted from the amino acid sequence. However, when the full length cDNA clone of castor bean PLD was expressed in *E. coli*, the resulting PLD protein exhibited a molecular weight of approximately 89,000, migrating faster than the PLD from castor bean endosperm (FIG. 3B). This result suggests that (I) the 30 amino acid leader peptide of the expressed PLD may be removed in *E. coli* and (ii) the PLD in castor bean may normally be post-translationally modified. A search for the consensus sequences of protein modifications identified several potential sites of phosphorylation by $Ca^{2+}$-calmodulin dependent protein kinase, protein kinase C, and tyrosine kinase (24). Biochemical evidence for the phosphorylation of PLD, however, remains to be reported.

Figure 4:
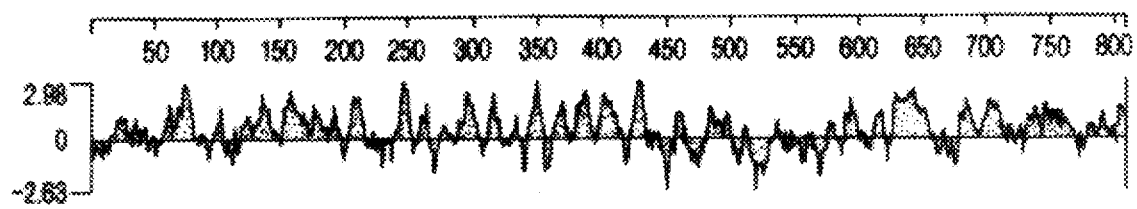
FIG. 4 is a computer-generated hydrophilicity plot of PLD carried out using a moving window of nine residues.

A secondary structure model for the PC-PLD has been deduced, which predicts a generally hydrophilic protein. A hydrophilicity plot (25) shows that most hydrophobic regions are scattered between residues 400–600 and that the N-terminal leader peptide is hydrophobic (see FIG. 4). The primary structure of the castor bean PLD does not contain a long stretch of non-polar residues (the longest is 5 residues at 513–518) nor any signals indicative of covalent lipid attachment reported for other organisms.

A computer search of the GenBank data base using the FASTA search program (26) identified that the N-terminal amino acid sequence of cabbage PLD (29 amino acids reported; 19) showed significant similarity with the castor bean PLD. The castor bean and cabbage PLD share 75% (21/28) amino acid identity. When conservative amino acid substitutions (K/R, F/T/W, N/Q, S/T, E/D, and V/I/L) were taken into account, the sequence similarity increased to 89% (25/28). Immunoblot analysis using the anti-PLD antibodies found that PLDs from various plant species possess common antigenic determinants (14). These results suggest that PLD sequences in plants may be highly conserved. Except for the partial cabbage PLD sequence, the predicted amino acid sequence of the PC-PLD had no significant identity to any sequence from GenBank reported to date.

Gene Expression

Figure 5:
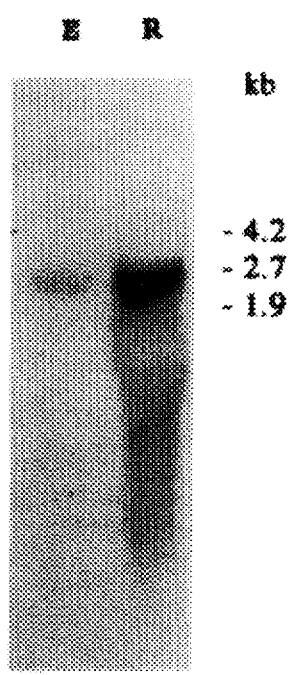
FIG. 5 is a photograph of a Northern blot analysis of RNA from castor bean.

Northern blot analysis of RNA derived from radicle and endosperm of 2-d postgermination castor bean revealed a single 2.7-kb band that hybridized with the 2.8-kb PLD probe (FIG. 5). In this experiment, total RNA (20 μg/lane) was electrophoresed through 1% agarose gel, transferred to a nylon membrane, and probed with a 2.8-kilobase pair PLD cDNA. RNA was isolated from endosperm (lane E) and radicle (lane R) of 2-d postgermination castor bean. The size of the message is in agreement with that derived from the cDNA sequence. The apparent difference in the intensity of the bands from the endosperm and radicle suggests that the expression of PLD was much higher in radicle than in endosperm.

The molecular organization of the PLD gene in castor bean was determined by Southern hybridization analysis of genomic DNA digested with various restriction endonucleases. Digestion with EcoRI that does not cut the probe region produced two hybridization signals, while digestion with BamHI which cuts once in the probe region gave 2 hybridization signals (data not shown). The simple hybridization pattern at high stringency suggests that castor bean genome may contain one or two gene copies of the PC-PLD. The pattern of hybridization at lower stringency shows a more complex pattern of signals suggestive of the presence of related gene families (data not shown).

DISCUSSION

The identity of the cDNA clone as castor bean PLD has been established by several lines of independent evidence. (I) Expression of this clone in *E. coli*, an organism in which PLD activity was undetectable under the present assay conditions, results in high levels of PLD activity. (ii) The deduced amino acid sequence of the cDNA is in perfect agreement with the chemically determined N-terminal amino acid sequence of the purified castor bean PLD and exhibits significant similarity to the N-terminal sequence of cabbage PLD. (iii) The protein expressed from the cDNA in *E. coli* is recognized by anti-PLD antibodies.

Introduction of the PLD cDNA clone into *E. coli* results in the synthesis of a protein capable of catalyzing both hydrolysis and transphosphatidylation reactions. The ability of transferring the phosphatidyl moiety to a primary alcohol is characteristic of PLDs from plants and animals, and the two reactions are generally considered to be mediated by the same protein based on biochemical studies (13). However, it had not been unambiguously demonstrated if the two reactions are catalyzed by the same polypeptide. Some studies have suggested that two active sites on one enzyme or two separate polypeptides are involved in the two reactions (27). The present results using the cloned PLD expressed in *E. coli* provide conclusive evidence that both the hydrolysis and transphosphatidylation reactions are catalyzed by one single PLD protein.

Nucleotide sequencing analysis indicates that a stretch of 30 amino acid residues precedes the mature N-terminal amino acid sequence determined directly from the purified PLD. It is likely that the leader peptide is removed during PLD maturation. This notion is supported by the fact that the N-terminal amino acid sequence of the purified cabbage PLD shares substantial sequence similarity with that of the mature castor bean PLD. Expression of the full length cDNA clone in *E. coli* results in the production of catalytically active PLD whereas expression of PLD without the leader sequence leads to the accumulation of a non-functional protein. The PLD expressed from the full cDNA is well protected from host cell proteolytic cleavage. On the other hand, the expression of PLD cDNA without the leader sequence produced a number of polypeptides which were smaller than the fusion protein and yet immunoreactive to anti-PLD antibodies, suggesting that these polypeptides were derived from the degradation of the expressed PLD. Based on these observations, it is suggested that this leader peptide is involved in proper folding of PLD to form functional PLD and protect it from degradation.

The 30 N-terminal amino acid peptide may also serve as a transit signal peptide. This sequence, however, lacks a stretch of core hydrophobic residues required for endomembrane targeting and also the distinct regions of transit peptides for mitochondria (28). It starts with Met-Ala, is positively charged, and is relatively rich in hydroxylated amino acids (T+S=5/30), all of which are the characteristics for plastid targeting peptides (28). However, the intracellular location of PLD is yet to be established. Plant PLD has been reported to be soluble in cytoplasm and associated with plastids, endoplasmic reticulum, mitochondrial membranes, and protein bodies, depending upon sources and types of tissues studied (5, 12, 18). Our recent immunocytochemical localization of PLD in castor bean tissues has found that PLD is present mostly in vacuoles, endoplasmic reticulum, some in plastids and plasma membrane, but little in mitochondria, Golgi apparatus, and glyoxysomes. Whether or not the leader peptide is able to target protein into plastids or vacuoles remain to be shown by direct evidence from protein import studies.

The sequences of two enzymes that hydrolyze the same terminal phosphodiesteric bond of other phospholipids have been reported: a phosphatidylinositol-glycan-specific PLD from bovine serum (29) and a sphingomyelin-hydrolyzing PLD from the gram-positive bacterium *Corynebacterium pseudotuberculosis* (30). The size of the castor bean PLD is comparable to that of the bovine phosphatidylinositol-glycan-specific PLD which is comprised of 817 amino acids (90.2 kD) plus a signal peptide of 23 amino acids. Comparison of the castor bean PLD with the bovine PLD did not identify any significant sequence similarity. No conserved sequences have been observed among the castor bean, bovine, and bacterial PLD. The lack of sequence similarity may reflect the fact that these PLDs are specific for the head groups of phospholipids. The cloned bovine phosphatidylinositol-glycan PLD does not hydrolyze PC (29). Although the cloned castor bean PLD has not been tested for its activity on phosphatidylinositol-glycan, previous studies with the purified castor bean PLD found that the castor bean PC-hydrolyzing PLD even failed to use phosphatidylinositol as substrate (15). Except for the homology found between the castor bean PLD and partial cabbage PLD sequences, database searches against the castor bean PLD sequence did not detect significant similarity with the nucleotide and protein sequences of other lipolytic enzymes.

REFERENCES

1. Billah, M. M. (1993) *Current Opinion in Immunology* 5, 114–123
2. Brown, H. A., Gutowski, S., Moomaw, C. R., Slaughter, C., and Sternweis, P. C. (1993) *Cell* 1993, 75, 1137–1144
3. Cockroft, S., Thomas, G. M. H., Fensome, A., Geny, B., Cunningham, E., Gout, I., Hiles, I., Totty, N. F., Truong, O., and Hsuan, J. J. (1994) *Science* 263, 523–526
4. Liscovitch, M. (1992) *Trends in Biochem. Sci.* 17, 393–399
5. Herman, E. M., and Chrispeels, M. J. (1980) *Plant Physiol.* 66, 1001–1007
6. Lee, M. H. (1989) *Plant Sci.* 59, 35–43
7. Borochov, A., Halevy, A., and Shinitzky, M. (1982) *Plant Physiol.* 69, 296–299
8. Brown, J. H., Chamber, J. A., and Thompson, J. E. (1990) *Phytochem.* 30, 2537–2542
9. Willemot, C. (1983) *Phytochem.* 22, 861–863
10. Voisine, R., Vezina, L-P., and Willemot, C. (1993) *Plant Physiol* 102, 213–218
11. Acharya, M. K., Dureja-Munjal, I., and Guha-Mukherjee, S. (1991) *Phytochem.* 30, 2895–2897
12. Wang, X. (1993) in *Lipid Metabolism in Plants*. (Moore, T. S. ed) pp 499–520, CRC Press, Boca Raton
13. Heller, M. (1978) *Adv. Lipid Res.* 16, 267–326
14. Wang, P., Athens, J. C., Sigel, M. L., Egan, R. W., and Billah, M. M. (1991) *J. Biol. Chem.* 266, 14877–14880
15. Dyer, J. H., Ryu, S. B., and Wang, X. (1994) *Plant Physiol* 105, in press
16. Heller, M., Mozes, N., Peri, I., and Maes, E. (1974) *Biochim. Biophy. Acta* 369, 397–410
17. Allgyer, T. T., and Wells, M. A. (1979) *Biochem.* 24, 5348–5353
18. Wang, X., Dyer, J. H., and Zheng, L. (1993) *Arch. Bichem. Biophys.* 306, 496–494
19. Abousalham, A., Reviere, M., Teissere, M., and Verger, R. (1993) *Biochim Biophys. Acta* 1158, 1–7
20. Wang, X., Bookjans, G., Altsuler, M., Collins, G. B. and Hildebrand, D. F. (1988) *Physiol. Plant.* 72, 127–132
21. Touchstone, J. C. Levin, S. S. Dobbins, M. F., and Carter, P. J. (1981) *J. High Res. Chrom. & Chrom. Commun.* 4, 423–424
22. Heidecker G. and Messing J. (1986) *Ann. Rev. Plant Physiol.* 37, 439–466
23. Lutcke H. A., Chow, K. C., Mikcel, F. S., Moss, K. A., Kern H. F. and Sheele, G. A. (1987) *EMBO J.* 6, 43–48
24. Aitken, A. (1990) *Identification of Protein Consensus Sequences: active site motifs, phosphorylation, and other post-translational modifications*, Ellis Horwood, London
25. Kyte, J. and Doolittle, R. F. (1982) *J. Mol. Biol.* 157, 105–132 2444–2448
26. Pearson, W. and Lipman, D. (1988) *Proc. Natl. Acad. Sci. USA* 85,
27. Saito, M., Bourque, E., and Kanfer, J. (1974) *Arch. Biochem. Biophys.* 164, 420–428
28. von Heijne, G., Steppuhn, J., and Herrmann, R. G. (1989) *Eur. J. Biochem.* 180, 535–545
29. Scallon, B. J., Fung, W.-J., Tsang, T. S., Li, S., Kado-Fong, H., Huang, K.-S., and Kochan, J. P. (1991) *Science* 252, 446–448
30. Hodgson, A. L. M., Bird, P., and Nisbet, L. I. (1990) *J. Bacteriol.* 172, 1256–1261

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2834 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:1:

```
GGCACGAGCT TCGTTTCACA TTCTCTGTAC TTTTACGATT ACGCGCATAC AAAATTATTT      60
TATTTGATAT ATACATACAC ACGGAGCTAA GATCGGATCA GATCACAGAA ATTCTCTCAT     120
TCTCAGATCT CTCTCTGTTT CTCTTCATCA TCATAAATTT ACAAGTGAGA AATGGCGCAG     180
ATATCTTTGC ACGGAACTCT ACATGTAACG ATCTATGAGG TGGATAAGCT TCACAGCGGA     240
GGTGGTCCCC ACTTCTTTCG TAAGCTTGTT GAAATATTG AGGAGACAGT TGGTTTTGGC      300
AAAGGAGTTA GTAAACTCTA TGCAACTATT GACCTAGAAA GGCTAGAGT TGGGAGGACT      360
AGAATACTGG AAAATGAACA ATCCAACCCC AGGTGGTATG AGTCCTTTCA CGTTTATTGT     420
GCTCATCAGG CTTCAAATGT AATATTCACA GTCAAGGATG ATAATCCTAT TGGGCCCACC     480
TTAATTGGAA GAGCATATGT ACCAGTTGAA GAGCTCCTAG ATGGAGAAGA GATAGATAGG     540
TGGGTTGAGA TATTGGATGA AGACAAGAAC CCCGTCCATA GTGGTTCTAA GATCCATGTG     600
AAACTGCAGT ACTTTGAGGT TACCAAGGAC CGTAACTGGG GACAGGGTAT CAGAAGTTCA     660
AAATATCCTG GAGTACCTTA TACATACTTC TCGCAGAGAC AAGGATGTAA GGTTTCTCTC     720
TACCAAGATG CTCATATTCC AGACAAATTT GTTCCTCAAA TTCCTCTTGC TGGAGGCAAT     780
TACTATGAGC CTCACAGGTG CTGGGAAGAT GTTTTTGATG CAATTACCAA TGCAAACAC      840
TTGATCTACA TCACTGGCTG GTCTGTTTAT ACTGAAATCT CCTTAATAAG GGACTCGAGG     900
AGGCCAAAGC CAGGAGGAGA TATCACCCTA GGTGAGCTGC TTAAGAAGAA GGCAAGTGAA     960
GGTGTTAGGG TCCTTATGCT GGTGTGGGAT GACAGAACCT CCGTTGGTTT ATTGAAAAAG    1020
GATGGACTCA TGGCAACTCA TGATGAGGAG ACTGAACATT TCTTCCAGAA TACTGATGTG    1080
CATTGTGTGC TGTGTCCTCG AAATCCTGAT GATGGTGGAA GCTTTGTTCA GGATCTACAA    1140
ATCTCTACTA TGTTCACTCA TCACCAGAAG ATTGTGGTGG TGGACAGTGC AATGCCTAAT    1200
GGAGATTCGC AGAGGAGGAG AATTGTCAGT TTTGTTGGGG GTCTCGACCT CTGTGATGGG    1260
AGATATGATT CCCCATTCCA TTCCCTTTTC AGGACACTGG ATTCGGCACA CCATGATGAT    1320
TTTCATCAGC CCAACTTTGC TGGTGCTTCA ATTGAAAAAG GTGGTCCAAG AGAACCTTGG    1380
CATGACATCC ACTCCAGACT GAAGGACCA ATTGCTTGGG ATGTTTGTT TAATTTTGAG      1440
CAGAGATGGA GAAAGCAAGG TGGTAAAGAC CTGCTCATTC AGCTGAGAGA ACTAGAAGAT    1500
GTTATCATTC CCCATCTCCT GTTATGCTAT CCTGATGACT TGAGGCATGG AATGTCCAGT    1560
TGTTTAGATC CATTGATGGT GGAGCTGCAT TTGGTTTCCC TGAGACACCT GAAGATGCGC    1620
CAGAGGCTGG GCTTGTACAG TGGAAAGGAT AACATCATTG ACCGAAGTAT TCAGATGCTT    1680
```

-continued

```
ATATCCATGC CATTCGAAGG GCAAAGAATT TTATTTATAT TGAAAATCAG TATTTCCTTG      1740
GAAGTTCTTT TTGGTTGGAG TCCTGATGGT ATTAAGCCTG AGGATATTAA TGCACTGCAT      1800
CTAATACCCA AGGAACTTTC ACTCAAGATA CTTAGCAAGA TTGCGGCAGG GGAGAGGTTC      1860
ACTGTTTACA TTGTTGTTCC AATGTGGCCA GAGGGTATAC CAGAGAGTGC ATCAGTTCAG      1920
GCTATATTAG ATTGGCAGAA GAGGACAATG GAAATGATGT ATAAGATAT  TGTGCAGGCT      1980
CTCAAAGCCA ATGGAATTAT TGAGGATCCT CGGAACTATC TGACATTCTT CTGCCTTGGT      2040
AACCGCGAAG TGAAGAAGAG TGGTGAATAT GAACCTGCAG AAAAACCAGA GCCTGATACA      2100
GACTATATAA GAGCTCAGGA GGCCAGACGT TTCATGATTT ATGTTCATAC AAAGATGATG      2160
ATTGTCGATG ATGAGTACAT TATAATTGGA TCTGCCAACA TCAACCAGAG ATCAATGGAT      2220
GGTGCTAGAG ACTCCGAAAT AGCCATGGGA GCCTATCAAC CACATCACTT GTCAACCAGG      2280
CAGCCAGCAC GAGGTCAGAT CCATGGTTTC CGTATGTCAT TATGGTACGA ACACCTTGGC      2340
ATGCTCGACG AGTCATTCCT TAATCCAGAA AGTGAGGAGT GTGTCAGAAA GGTGAACCAG      2400
ATGGCAGAAA ATATTGGGA  TCTCTATTCA AGCGAGACAC TGGAACATGA CCTACCTGGT      2460
CATTTGCTCC GGTATCCTAT TGGGGTCGCT AGTGAAGGAG ATGTCACAGA GCTCCCTGGA      2520
ACCGAGTTTT TCCCTGACAC GAAGGCTCGT GTTCTAGGTG CTAAATCCGA TTACCTTCCT      2580
CCCGATCCTG ACACTTAATG GAACTCTAAG CAGTTCTCGA AGAATTACCT GCCTTGCCAG      2640
CCCATTTATG TTACTAGTTG TAGCCAGAAA ATAAATCATG TATCGCCATT CTATCCATAA      2700
TGTTTTTGTG CCAGGATTGG GGTATCAGGA TTGACAGATG TGTCACTGCT GTGGTGTGGT      2760
GTGATGCTGT CTATGTTGAA CTTTGTTTAT CTAATCCATG TCTTTTCTA  CAAAACAAAA      2820
AAAAAAAAAA AAAA                                                       2834
```

(2) INFORMATION FOR SEQ ID NO:2:

(i) SEQUENCE CHARACTERISTICS:
        (A) LENGTH: 808 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:2:

```
Met Ala Gln Ile Ser Leu His Gly Thr Leu His Val Thr Ile Tyr Glu
 1               5                  10                  15

Val Asp Lys Leu His Ser Gly Gly Pro His Phe Phe Arg Lys Leu
            20                  25                  30

Val Glu Asn Ile Glu Glu Thr Val Gly Phe Gly Lys Gly Val Ser Lys
                35                  40                  45

Leu Tyr Ala Thr Ile Asp Leu Glu Lys Ala Arg Val Gly Arg Thr Arg
        50                  55                  60

Ile Leu Glu Asn Glu Gln Ser Asn Pro Arg Trp Tyr Glu Ser Phe His
 65                 70                  75                  80

Val Tyr Cys Ala His Gln Ala Ser Asn Val Ile Phe Thr Val Lys Asp
                85                  90                  95

Asp Asn Pro Ile Gly Pro Thr Leu Ile Gly Arg Ala Tyr Val Pro Val
            100                 105                 110

Glu Glu Leu Leu Asp Gly Glu Glu Ile Asp Arg Trp Val Glu Ile Leu
        115                 120                 125

Asp Glu Asp Lys Asn Pro Val His Ser Gly Ser Lys Ile His Val Lys
```

-continued

|  | | 130 | | | | 135 | | | | | 140 | | | |
|---|---|---|---|---|---|---|---|---|---|---|---|---|---|---|
| Leu | Gln | Tyr | Phe | Glu | Val | Thr | Lys | Asp | Arg | Asn | Trp | Gly | Gln | Gly | Ile |
| 145 | | | | | 150 | | | | 155 | | | | | 160 |
| Arg | Ser | Ser | Lys | Tyr | Pro | Gly | Val | Pro | Tyr | Thr | Tyr | Phe | Ser | Gln | Arg |
| | | | | 165 | | | | 170 | | | | | 175 | |
| Gln | Gly | Cys | Lys | Val | Ser | Leu | Tyr | Gln | Asp | Ala | His | Ile | Pro | Asp | Lys |
| | | | 180 | | | | | 185 | | | | | 190 | | |
| Phe | Val | Pro | Gln | Ile | Pro | Leu | Ala | Gly | Gly | Asn | Tyr | Tyr | Glu | Pro | His |
| | | | 195 | | | | 200 | | | | | 205 | | | |
| Arg | Cys | Trp | Glu | Asp | Val | Phe | Asp | Ala | Ile | Thr | Asn | Ala | Lys | His | Leu |
| | 210 | | | | | 215 | | | | | 220 | | | | |
| Ile | Tyr | Ile | Thr | Gly | Trp | Ser | Val | Tyr | Thr | Glu | Ile | Ser | Leu | Ile | Arg |
| 225 | | | | | 230 | | | | | 235 | | | | | 240 |
| Asp | Ser | Arg | Arg | Pro | Lys | Pro | Gly | Gly | Asp | Ile | Thr | Leu | Gly | Glu | Leu |
| | | | | 245 | | | | | 250 | | | | | 255 | |
| Leu | Lys | Lys | Lys | Ala | Ser | Glu | Gly | Val | Arg | Val | Leu | Met | Leu | Val | Trp |
| | | | 260 | | | | | 265 | | | | | 270 | | |
| Asp | Asp | Arg | Thr | Ser | Val | Gly | Leu | Leu | Lys | Lys | Asp | Gly | Leu | Met | Ala |
| | | | 275 | | | | | 280 | | | | | 285 | | |
| Thr | His | Asp | Glu | Glu | Thr | Glu | His | Phe | Phe | Gln | Asn | Thr | Asp | Val | His |
| | | 290 | | | | | 295 | | | | | 300 | | | |
| Cys | Val | Leu | Cys | Pro | Arg | Asn | Pro | Asp | Asp | Gly | Gly | Ser | Phe | Val | Gln |
| 305 | | | | | 310 | | | | | 315 | | | | | 320 |
| Asp | Leu | Gln | Ile | Ser | Thr | Met | Phe | Thr | His | His | Gln | Lys | Ile | Val | Val |
| 1 | | | | 325 | | | | | 330 | | | | | 335 | |
| Val | Asp | Ser | Ala | Met | Pro | Asn | Gly | Asp | Ser | Gln | Arg | Arg | Arg | Ile | Val |
| | | | 340 | | | | | 345 | | | | | 350 | | |
| Ser | Phe | Val | Gly | Gly | Leu | Asp | Leu | Cys | Asp | Gly | Arg | Tyr | Asp | Ser | Pro |
| | | 355 | | | | | 360 | | | | | 365 | | | |
| Phe | His | Ser | Leu | Phe | Arg | Thr | Leu | Asp | Ser | Ala | His | His | Asp | Asp | Phe |
| | 370 | | | | | 375 | | | | | 380 | | | | |
| His | Gln | Pro | Asn | Phe | Ala | Gly | Ala | Ser | Ile | Glu | Lys | Gly | Gly | Pro | Arg |
| 385 | | | | | 390 | | | | | 395 | | | | | 400 |
| Glu | Pro | Trp | His | Asp | Ile | His | Ser | Arg | Leu | Glu | Gly | Pro | Ile | Ala | Trp |
| | | | | 405 | | | | | 410 | | | | | 415 | |
| Asp | Val | Leu | Phe | Asn | Phe | Glu | Gln | Arg | Trp | Arg | Lys | Gln | Gly | Gly | Lys |
| | | | 420 | | | | | 425 | | | | | 430 | | |
| Asp | Leu | Leu | Ile | Gln | Leu | Arg | Glu | Leu | Glu | Asp | Val | Ile | Ile | Pro | His |
| | | 435 | | | | | 440 | | | | | 445 | | | |
| Leu | Leu | Leu | Cys | Tyr | Pro | Asp | Asp | Leu | Arg | His | Gly | Met | Ser | Ser | Cys |
| | 450 | | | | | 455 | | | | | 460 | | | | |
| Leu | Asp | Pro | Leu | Met | Val | Glu | Leu | His | Leu | Val | Ser | Leu | Arg | His | Leu |
| 465 | | | | | 470 | | | | | 475 | | | | | 480 |
| Lys | Met | Arg | Gln | Arg | Leu | Gly | Leu | Tyr | Ser | Gly | Lys | Asp | Asn | Ile | Ile |
| | | | | 485 | | | | | 490 | | | | | 495 | |
| Asp | Arg | Ser | Ile | Gln | Met | Leu | Ile | Ser | Met | Pro | Phe | Glu | Gly | Gln | Arg |
| | | | 500 | | | | | 505 | | | | | 510 | | |
| Ile | Leu | Phe | Ile | Leu | Lys | Ile | Ser | Ile | Ser | Leu | Glu | Val | Leu | Phe | Gly |
| | | 515 | | | | | 520 | | | | | 525 | | | |
| Trp | Ser | Pro | Asp | Gly | Ile | Leu | Pro | Glu | Asp | Ile | Asn | Ala | Leu | His | Leu |
| | 530 | | | | | 535 | | | | | 540 | | | | |
| Ile | Pro | Lys | Glu | Leu | Ser | Leu | Lys | Ile | Leu | Ser | Lys | Ile | Ala | Ala | Gly |
| 545 | | | | | 550 | | | | | 555 | | | | | 560 |

|      |      |      |      |            |      |      |      |      |            |      |      |      |      |            |
|------|------|------|------|------------|------|------|------|------|------------|------|------|------|------|------------|
| Glu  | Arg  | Phe  | Thr  | Val<br>565 | Tyr  | Ile  | Val  | Val  | Pro<br>570 | Met  | Trp  | Pro  | Glu  | Gly<br>575 | Ile  |
| Pro  | Glu  | Ser  | Ala<br>580 | Ser  | Val  | Gln  | Ala  | Ile<br>585 | Leu  | Asp  | Trp  | Gln  | Lys<br>590 | Arg  | Thr  |
| Met  | Glu  | Met<br>595 | Met  | Tyr  | Lys  | Asp  | Ile<br>600 | Val  | Gln  | Ala  | Leu  | Lys<br>605 | Ala  | Asn  | Gly  |
| Ile  | Ile<br>610 | Glu  | Asp  | Pro  | Arg  | Asn<br>615 | Tyr  | Leu  | Thr  | Phe  | Phe<br>620 | Cys  | Leu  | Gly  | Asn  |
| Arg<br>625 | Glu  | Val  | Lys  | Lys  | Ser<br>630 | Gly  | Glu  | Tyr  | Glu  | Pro<br>635 | Ala  | Glu  | Lys  | Pro  | Glu<br>640 |
| Pro  | Asp  | Thr  | Asp  | Tyr<br>645 | Ile  | Arg  | Ala  | Gln  | Glu<br>650 | Ala  | Arg  | Arg  | Phe  | Met<br>655 | Ile  |
| Tyr  | Val  | His  | Thr<br>660 | Lys  | Met  | Met  | Ile  | Val<br>665 | Asp  | Asp  | Glu  | Tyr  | Ile<br>670 | Ile  | Ile  |
| Gly  | Ser  | Ala<br>675 | Asn  | Ile  | Asn  | Gln  | Arg<br>680 | Ser  | Met  | Asp  | Gly  | Ala<br>685 | Arg  | Asp  | Ser  |
| Glu  | Ile<br>690 | Ala  | Met  | Gly  | Ala  | Tyr<br>695 | Gln  | Pro  | His  | His  | Leu<br>700 | Ser  | Thr  | Arg  | Gln  |
| Pro<br>705 | Ala  | Arg  | Gly  | Gln  | Ile<br>710 | His  | Gly  | Phe  | Arg  | Met<br>715 | Ser  | Leu  | Trp  | Tyr  | Glu<br>720 |
| His  | Leu  | Gly  | Met  | Leu<br>725 | Asp  | Glu  | Ser  | Phe  | Leu<br>730 | Asn  | Pro  | Glu  | Ser  | Glu<br>735 | Glu  |
| Cys  | Val  | Arg  | Lys<br>740 | Val  | Asn  | Gln  | Met  | Ala<br>745 | Glu  | Lys  | Tyr  | Trp  | Asp<br>750 | Leu  | Tyr  |
| Ser  | Ser  | Glu<br>755 | Thr  | Leu  | Glu  | His  | Asp<br>760 | Leu  | Pro  | Gly  | His  | Leu<br>765 | Leu  | Arg  | Tyr  |
| Pro  | Ile<br>770 | Gly  | Val  | Ala  | Ser  | Glu<br>775 | Gly  | Asp  | Val  | Thr  | Glu<br>780 | Leu  | Pro  | Gly  | Thr  |
| Glu<br>785 | Phe  | Phe  | Pro  | Asp  | Thr<br>790 | Lys  | Ala  | Arg  | Val  | Leu<br>795 | Gly  | Ala  | Lys  | Ser  | Asp<br>800 |
| Tyr  | Leu  | Pro  | Pro  | Asp<br>805 | Pro  | Asp  | Thr  |      |            |      |      |      |      |            |      |

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GARGARACNG TNGGNTT Y GG NAARGGNGT 29

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

Y TNTA Y GCNA CNAT-
NGAK Y T 20

I claim:
1. A recombinant DNA sequence, wherein the DNA sequence encodes a phospholipase D, and hybridizes to an oligonucleotide when the DNA sequence and the oligonucleotide are held at 59° C. for 18 hours in a solution including 6X SSC, 10 mM $(Na)_3PO_4$, 1 mM EDTA, 0.5% SDS, 0.1% nonfat dried milk, and 50 µg/ml denatured salmon sperm DNA, wherein the oligonucleotide is selected from the group consisting of GARGARACNGTNGGNTTYG-GNAARGGNGT (SEQ ID #3) and YTNTAYGCNAC-NATNGAKYT (SEQ ID #4), wherein N is inosine, R is A or G, Y is T or C, and K is T or G.

2. The DNA sequence of claim 1, wherein the DNA sequence is a cDNA sequence.

3. The DNA sequence of claim 1, the DNA sequence is derived from a plant.

4. The DNA sequence of claim 3, wherein the plant is castor bean.

5. The DNA sequence of claim 1, wherein the DNA sequence encodes the protein encoded by SEQ ID #1.

6. The DNA sequence of claim 5, wherein the DNA sequence includes the protein-coding sequence present in SEQ ID #1.

7. A vector comprising a recombinant DNA sequence, wherein the DNA sequence encodes a phospholipase D, and hybridizes to an oligonucleotide when the DNA sequence and the oligonucleotide are held at 59° C. for 18 hours in a solution including 6X SSC, 10 mM (Na)$_3$PO$_4$, 1 mM EDTA, 0.5% SDS, 0.1% nonfat dried milk, and 50 µg/ml denatured salmon sperm DNA, wherein the oligonucleotide is selected from the group consisting of GARGARACNGTNGGNTTYG-GNAARGGNGT (SEQ ID #3) and YTNTAYGCNAC-NATNGAKYT (SEQ ID #4), wherein N is inosine, R is A or G, Y is T or C, and K is T or G.

8. The vector of claim 7, wherein the vector is an expression vector.

9. The vector of claim 7, wherein the vector is selected from the group consisting of a phage λ vector and a plasmid vector.

10. The vector of claim 7, wherein the DNA sequence is a cDNA sequence.

11. The vector of claim 7, wherein the DNA sequence is derived from a plant.

12. The vector of claim 11, wherein the plant is castor bean.

13. The vector of claim 7, wherein the DNA sequence encodes the protein encoded by SEQ ID #1.

14. The vector of claim 13, wherein the DNA sequence includes the protein-coding sequence present in SEQ ID #1.

15. A cell comprising a recombinant DNA sequence, wherein the DNA sequence encodes a phospholipase D, and hybridizes to an oligonucleotide when the DNA sequence and the oligonucleotide are held at 59° C. for 18 hours in a solution including 6X SSC, 10 mM (Na)$_3$PO$_4$, 1 mM EDTA, 0.5% SDS, 0.1% nonfat dried milk, and 50 µg/ml denatured salmon sperm DNA, wherein the oligonucleotide is selected from the group consisting of GARGARACNGTNGGNTTYG-GNAARGGNGT (SEQ ID #3) and YTNTAYGCNAC-NATNGAKYT (SEQ ID #4), wherein N is inosine, R is A or G, Y is T or C, and K is T or G.

16. The cell of claim 15, wherein the cell is a procaryotic cell.

17. The cell of claim 15, wherein the DNA sequence is a cDNA sequence.

18. The cell of claim 15, wherein the DNA sequence is included in a vector.

19. The cell of claim 17, wherein the vector is an expression vector.

20. The cell of claim 18, wherein the vector is selected from the group consisting of a phage λ vector and a plasmid vector.

21. The cell of claim 15, wherein the DNA sequence is derived from a plant.

22. The cell of claim 21, wherein the plant is castor bean.

23. The cell of claim 15, wherein the DNA sequence encodes the protein encoded by SEQ ID #1.

24. The cell of claim 15, wherein the DNA sequence includes the protein-coding sequence present in SEQ ID #1.

* * * * *